United States Patent
Zeetser et al.

(10) Patent No.: US 8,998,904 B2
(45) Date of Patent: Apr. 7, 2015

(54) WINGED TETHER PLATE AND METHOD OF USE FOR REDUCING ANGULAR BONE DEFORMITY

(71) Applicants: Vladimir Zeetser, Tarzana, CA (US); Dawn Buratti, Malibu, CA (US)

(72) Inventors: Vladimir Zeetser, Tarzana, CA (US); Dawn Buratti, Malibu, CA (US)

(73) Assignee: FastForward Surgical Inc., Henderson, NV (US)

( * ) Notice: Subject to any disclaimer, the term of this patent is extended or adjusted under 35 U.S.C. 154(b) by 0 days.

(21) Appl. No.: 13/720,826

(22) Filed: Dec. 19, 2012

(65) Prior Publication Data

US 2014/0025123 A1    Jan. 23, 2014

Related U.S. Application Data

(60) Provisional application No. 61/672,297, filed on Jul. 17, 2012, provisional application No. 61/713,443, filed on Oct. 12, 2012.

(51) Int. Cl.
| | |
|---|---|
| *A61B 17/56* | (2006.01) |
| *A61B 17/58* | (2006.01) |
| *A61B 17/82* | (2006.01) |
| *A61F 2/30* | (2006.01) |
| *A61B 17/80* | (2006.01) |

(52) U.S. Cl.
CPC .......... *A61B 17/8061* (2013.01); *A61B 17/8033* (2013.01); *A61B 17/8085* (2013.01); *A61B 17/82* (2013.01); *Y10S 606/902* (2013.01); *Y10S 606/906* (2013.01)

(58) Field of Classification Search
CPC ...... A61B 17/80; A61B 17/82; A61B 17/842; A61B 2/42; A61B 2/4225; A61B 2/4241
USPC .............. 606/280–299, 70, 71, 74, 232, 233, 606/902–906; 623/21.11–21.19, 13.11, 623/13.12
See application file for complete search history.

(56) References Cited

U.S. PATENT DOCUMENTS

| | | |
|---|---|---|
| 1,665,030 A | 4/1928 | Hartwig |
| 1,746,865 A | 2/1930 | Page |
| 2,596,038 A | 5/1952 | Mayer |

(Continued)

FOREIGN PATENT DOCUMENTS

| | | |
|---|---|---|
| WO | WO 2008/019511 A1 | 2/2008 |
| WO | WO 2009/086397 A2 | 7/2009 |

OTHER PUBLICATIONS

International Search Report and Written Opinion in Application No. PCT/US2013/050687, mailed Sep. 6, 2013, 15 pages.

(Continued)

*Primary Examiner* — Matthew Lawson
*Assistant Examiner* — Si Ming Lee
(74) *Attorney, Agent, or Firm* — Knobbe, Martens, Olson & Bear, LLP

(57) ABSTRACT

The present invention is a method and device for the correction and reduction of bone deformities, such as metatarsus primus adductus, using a plate body with winged buttresses and dorsal loop. The method and device can be affixed to a bone without any drilling or violating of the bone and can use a tethering technique which does not require drilling into the second metatarsal, nor does it require the placement of a prominent suture knot/button device medially along the first metatarsal.

21 Claims, 6 Drawing Sheets

(56) References Cited

U.S. PATENT DOCUMENTS

| | | | |
|---|---|---|---|
| 2,706,023 A * | 4/1955 | Merritt | 52/148 |
| 2,958,324 A | 11/1960 | Berkemann | |
| 4,583,303 A | 4/1986 | Laiacona et al. | |
| 4,644,940 A | 2/1987 | Nakamura | |
| 5,190,545 A * | 3/1993 | Corsi et al. | 606/74 |
| 5,282,782 A | 2/1994 | Kasahara | |
| 5,529,075 A | 6/1996 | Clark | |
| 5,743,913 A | 4/1998 | Wellisz | |
| 5,843,085 A | 12/1998 | Graser | |
| 6,318,373 B1 | 11/2001 | Kasahara | |
| 6,391,031 B1 | 5/2002 | Toomey | |
| 6,520,965 B2 * | 2/2003 | Chervitz et al. | 606/74 |
| 6,629,943 B1 | 10/2003 | Schroder | |
| 6,746,450 B1 * | 6/2004 | Wall et al. | 606/280 |
| 6,964,645 B1 | 11/2005 | Smits | |
| 7,344,538 B2 | 3/2008 | Myerson et al. | |
| 7,582,088 B2 | 9/2009 | Marissen et al. | |
| 7,875,058 B2 | 1/2011 | Holmes | |
| 7,901,431 B2 | 3/2011 | Shumas | |
| 8,057,522 B2 * | 11/2011 | Rothman et al. | 606/289 |
| 8,221,455 B2 | 7/2012 | Shumas | |
| 8,257,403 B2 | 9/2012 | Den Hartog et al. | |
| 8,257,406 B2 | 9/2012 | Kay et al. | |
| 8,398,678 B2 | 3/2013 | Baker et al. | |
| 2004/0127907 A1 | 7/2004 | Dakin et al. | |
| 2005/0021033 A1 | 1/2005 | Zeiler et al. | |
| 2005/0049593 A1 | 3/2005 | Duong et al. | |
| 2006/0241607 A1 | 10/2006 | Myerson et al. | |
| 2006/0241608 A1 | 10/2006 | Myerson et al. | |
| 2008/0008777 A1 | 1/2008 | Radovic | |
| 2008/0155731 A1 | 7/2008 | Kasahara | |
| 2008/0177302 A1 | 7/2008 | Shurnas | |
| 2008/0269806 A1 * | 10/2008 | Zhang et al. | 606/286 |
| 2009/0021001 A1 | 1/2009 | Strnad | |
| 2009/0036893 A1 | 2/2009 | Kartalian et al. | |
| 2009/0076617 A1 * | 3/2009 | Ralph et al. | 623/17.19 |
| 2009/0210010 A1 * | 8/2009 | Strnad et al. | 606/280 |
| 2009/0222047 A1 | 9/2009 | Graham | |
| 2009/0254190 A1 | 10/2009 | Gannoe et al. | |
| 2010/0036430 A1 | 2/2010 | Hartdegen et al. | |
| 2010/0094294 A1 * | 4/2010 | Gillard et al. | 606/74 |
| 2010/0094428 A1 * | 4/2010 | Ralph et al. | 623/17.19 |
| 2010/0106110 A1 | 4/2010 | De Luca | |
| 2010/0125297 A1 | 5/2010 | Guederian et al. | |
| 2010/0152752 A1 | 6/2010 | Denove et al. | |
| 2010/0211071 A1 | 8/2010 | Lettmann et al. | |
| 2010/0211075 A1 * | 8/2010 | Stone | 606/70 |
| 2010/0234896 A1 | 9/2010 | Lorenz et al. | |
| 2010/0249687 A1 | 9/2010 | Goswami et al. | |
| 2010/0262194 A1 | 10/2010 | Wagner et al. | |
| 2011/0061664 A1 | 3/2011 | Paris Mayans Carlos | |
| 2011/0077656 A1 | 3/2011 | Sand et al. | |
| 2011/0082405 A1 | 4/2011 | Domangue et al. | |
| 2011/0118780 A1 | 5/2011 | Holmes, Jr. | |
| 2011/0119807 A1 | 5/2011 | DellaCorte et al. | |
| 2011/0130789 A1 | 6/2011 | Shurnas et al. | |
| 2011/0178557 A1 | 7/2011 | Rush et al. | |
| 2011/0224729 A1 | 9/2011 | Baker | |
| 2011/0301648 A1 | 12/2011 | Lofthouse et al. | |
| 2012/0016426 A1 | 1/2012 | Robinson | |
| 2012/0071935 A1 | 3/2012 | Keith et al. | |
| 2012/0215147 A1 | 8/2012 | Lunnon | |
| 2012/0330322 A1 | 12/2012 | Sand et al. | |

OTHER PUBLICATIONS

Nov. 24, 2014, International Search Report and Written Opinion for International Application No. PCT/US2014/046824 Filed Jul. 16, 2014.

* cited by examiner

WINGED TETHER PLATE AND METHOD OF USE FOR REDUCING ANGULAR BONE DEFORMITY

CROSS-REFERENCE TO RELATED APPLICATION

This application claims the benefit of Provisional Application No. 61/672,297 filed on Jul. 17, 2012 and 61/713,443 filed on Oct. 12, 2012.

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

This invention relates to surgical implant devices for repairing angular bone deformities, in particular, metatarsus primus adductus. While the invention was conceived for the purposes of correcting metatarsus primus adductus, it is conceivable that the invention can be adapted to correct other bone deformities as long as there is a stable bone somewhat adjacent to an unstable bone.

Metatarsus primus adductus is a progressive angular deformity in the foot, between the first and second metatarsals, when the unstable or hypermobile first metatarsal deviates medially, increasing the intermetatarsal angle between the first and second metatarsals, Surgical procedures to correct this condition are chosen based on the severity of the angular deformity. Traditionally, surgical correction of moderate to severe angular deformities between the first and second metatarsals involves bone remodeling, osteotomies, wedge resection of bone or joint fusions, which cause irreversible alterations to bone and joint structures. A more desirable technique is to anatomically correct the deformity by reducing the abnormally wide angle between the two metatarsals by tethering them closer together using suture like material. Known are U.S. Pat. Nos. 8,221,455, 7,901,431, 7,875,058, 5,529,075, and U.S. patent application No. 20,110,224,729.

U.S. Pat. Nos. 8,221,455, 7,901,431, 7,875,058 and U.S. patent application No. 20,110,224,729 are tethering techniques whereby fiberwire, a suture-like material, along with buttress plates and/or buttons are used to tether the first and second metatarsals closer together like a tightrope. These techniques require holes to be drilled through both the first and second metatarsals. The Mini Tightrope system by Arthrex is an example of the tethering technique. First, a hole is drilled through the first and second metatarsals. Next, a buttress plate is secured to the second metatarsal bone by passing the suture through holes in the plate and through holes in both bones, then reducing the angular deformity by tightening the suture using a button and suture knot located on the medial side of the first metatarsal. The Mini Tightrope FT system by Arthrex is another example of tethering technique which uses an anchor-suture-button complex, where a threaded anchor is drilled into the second metatarsal base and the suture thread is then passed through a hole in the first metatarsal and the angular deformity is reduced as the suture thread is tightened and secured with a suture knot and button located along the medial aspect of the first metatarsal. Both of these tethering techniques require drilling into both the second and first metatarsals. U.S. Pat. No. 5,529,075 is similar in that it too requires drilling through the first and second metatarsals. Instead of a flexible suture-anchor technique, this reference requires the installation of a rigid stabilizing member between the first and second metatarsal. However, each of these references suffers from one or more of the following disadvantages: a hole must be drilled into or through the second metatarsal, to secure one end of the tethering device while the other (medial) end of the tethering device is secured with a button.

Drilling a hole through the second metatarsal, which is significantly smaller in diameter by comparison to the first metatarsal, severely weakens the bone. To minimize weakening of the second metatarsal, the hole must be drilled through the centerline of the bone so that a maximum amount of bone remains above and below the hole. Nevertheless, drilling a hole through the centerline of the second metatarsal is especially difficult because it is done at an angle through a hole in the first metatarsal. Making the procedure more difficult, the drilling must be done with little or no visibility. A second metatarsal bone which has been drilled through is more vulnerable to stress and/or fracture from tension caused by the tethering techniques. Fracture of the second metatarsal is a common and potentially devastating complication of these tethering techniques. Additionally, the use of buttons and suture knots located along the medial aspect of the first metatarsal can cause irritation of tissue, knot loosening and skin irritation/breakdown from prominent components.

Some surgeons have attempted to avoid drilling into the second metatarsal via a modification of the tethering technique, known as lasso technique. With the lasso technique, no holes are drilled through the second metatarsal, and no buttress plate or button is used. Instead, suture tape (i.e. Fibertape) is tied around the second metatarsal in the form of a cow-hitch knot and then secured to the first metatarsal. While the lasso technique avoids drilling through the second metatarsal by instead looping suture tape around the metatarsal, the suture tie itself can cause periosteal reaction and bone callus formation in some patients due to friction between the suture tape and the bone. To avoid periosteal reaction, few surgeons use absorbable suture to tether the first and second metatarsals together, but once the suture finally absorbs there is likely some loss of correction and possible recurrence of angular deformity.

Because of the aforementioned problems, there is a need for method and device for reducing angular bone deformities between two bones, using a tethering technique with a suture material which not only avoids the complications associated with drilling into the second metatarsal, but also avoids the friction and tension forces (i.e. rope-burn) associated with lasso-type techniques and which also avoids the complications associated with the prominent medial button and suture knot.

The present invention satisfies this need in the form of a method and device that allows for the correction and reduction of angular deformities such as metatarsus primus adductus using a tethering technique which does not require drilling into the second metatarsal, nor does it require the placement of a prominent suture knot/button device medially along the first metatarsal.

SUMMARY

The inventive device is a Winged Looped Plate comprising a plate body with winged buttresses and dorsal loop. The Winged Looped Plate with incorporated dorsal loop can be affixed to a bone without any drilling or violating of the bone. With the plate against the bone cortex, a cerclage technique can be used to loop cerclage material, such as suture tape, fibertape, or wire, around the plate and bone. The cerclage material is passed through the dorsal loop of the plate to keep the cerclage material centered on the plate. The cerclage material is tied around the second metatarsal using a lasso-type or cowhitch-type tie, Then, upon tightening the cerclage, the plate would be affixed to the bone under tension, thereby dispensing with the need to affix the plate to the bone with screws or drilled holes. The other end of the tethering mechanism can then be fixated to the first metatarsal (with the angular deformity anatomically reduced) using knotless anchors (interference screws) thus avoiding the use of prominent buttons and suture knots that are components of all other comparative tethering methods. By using a cerclage technique to affix the Winged Looped Plate to bone under tension, the second metatarsal is protected not only from drill hole related stress fractures, but also from friction/shear forces (cortical reaction) associated with tying suture around bone and directly against the bone cortex without any shielding.

This method and device addresses the aforementioned existing problem of angular bone deformities, in particular metatarsus primus adductus, the underlying cause of hallux valgus/bunion deformities, by utilizing the Winged Looped Plate of the present invention, placed directly against the second metatarsal bone.

The Winged Looped Plate allows the surgeon to tie cerclage material around the plate, protecting the bone from both friction and tension forces and eliminating need for drilling through the second metatarsal. The method uses the Winged Looped Plate, cerclage material, a suture passing instrument and two tenodesis (interference) screws to achieve a true reduction of the angular deformity. The two bones are tethered together using a cerclage technique with the Winged Looped Plate protecting the second metatarsal, while knotless anchors are used in the first metatarsal. This method creates a button-less, knotless, fully adjustable and reversible angular deformity correction, while the plate protects the second metatarsal bone from harmful tension and friction.

While the invention was conceived for the purposes of correcting metatarsus primus adductus, it is conceivable that the invention can be adapted to correct other bone deformities as long as there is a stable bone somewhat adjacent to an unstable bone.

DRAWINGS

Figure 10:
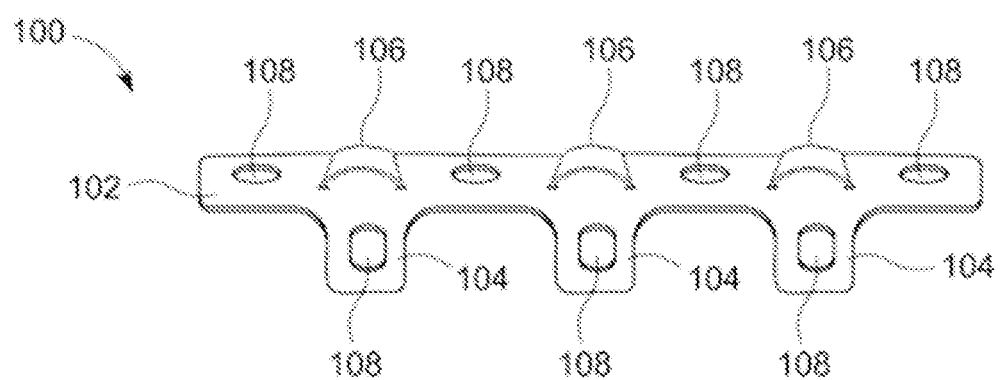

FIG. 10 is an alternate embodiment of the Winged Looped Plate device embodying features of the present invention for protection of a long bone when using any cerclage technique in a series as may be necessary for longer bones. An elongated version of the Winged Looped Plate allows for multiple wings and multiple loops for applying a series of cerclage ties over a longer bone. This figure also shows a possible low-profile variation of the loops if the cerclage material is thinner (i.e. monofilament wire).

Figure 11:
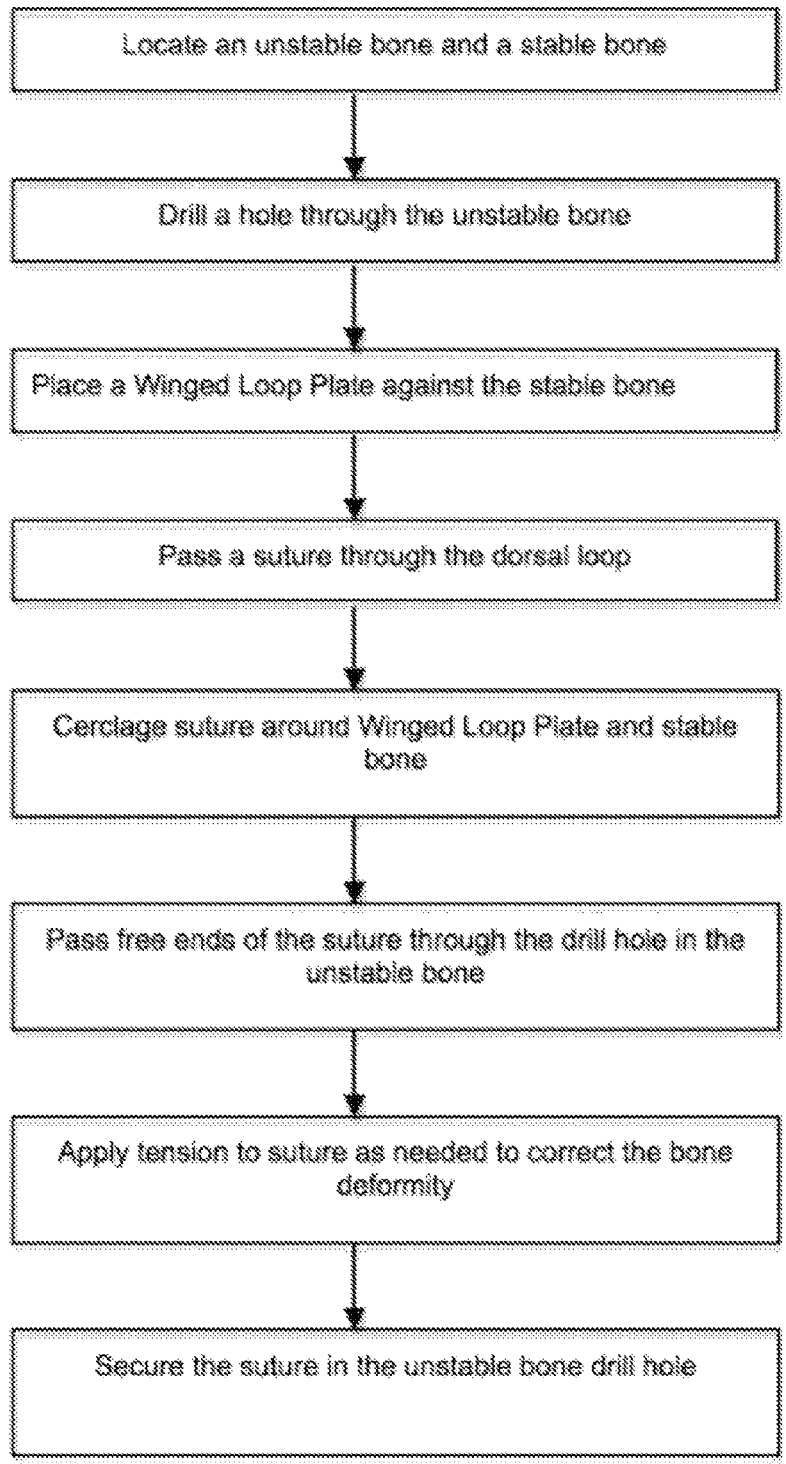

FIG. 11 is a flowchart illustrating a method of using the present invention for the correction of a bone deformity.

DESCRIPTION

Figure 1:
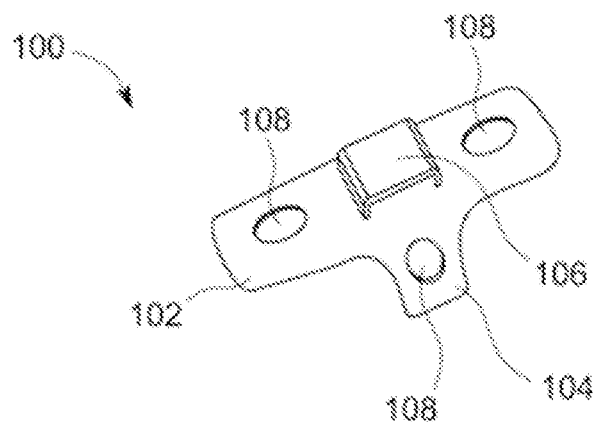
FIG. 1 is a perspective view of a device embodying features of the present invention for a method and device for correcting bone deformities such as metatarsus primus adductus.
Figure 2:
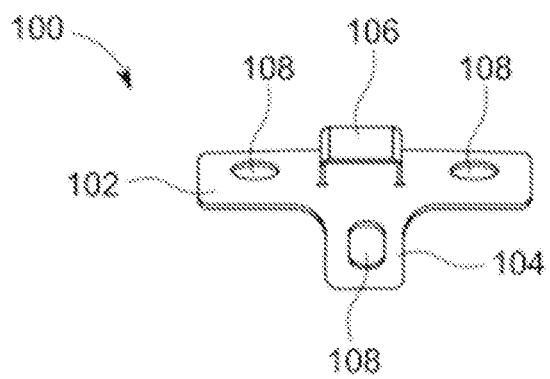
FIG. 2 is a side profile view of a device embodying features of the present invention for a method and device for correcting bone deformities such as metatarsus primus adductus.
Figure 3:
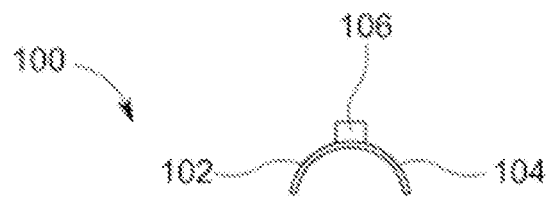
FIG. 3 is a front profile view of a device embodying features of the present invention for a method and device for correcting bone deformities such as metatarsus primus adductus.

FIGS. 1-3 illustrate the current embodiment of the Winged Looped Plate 100 device to correct bone deformities, in particular metatarsus primus adductus, the underlying cause of hallux valgus/bunion deformities. The Winged Looped Plate 100 comprises a plate body 102 which is semi-tubular but can also be tubular, with buttress wings 104, a dorsal loop 106, and ingrowth holes 108. Depending on where the plate is to be used, the number of buttress wings 104, the number and shape of the dorsal loops 106, and size and number of holes 108 on the plate body can be customized. For example, several sets of buttress wings 104, dorsal loops 106, and ingrowth holes 108 can be arranged in series along a plate body for use in longer bones when a series of cerclage ties are needed. (FIG. 10). The plate body 102 is semi-tubular in shape with a convex outer surface and concave inner surface to distribute forces of the suture tape evenly and avoid the need to drill a hole through the bone. The plate body 102 comprises extension buttress wings 104 which follow the semi-tubular shape of the plate body to protect the adjacent bone cortices where suture tape wraps around the device and bone. The plate body 102 and buttress wings 104 may have ingrowth holes 108 to allow bony and soft tissue/scar tissue ingrowth for long-term fixation and stability of the plate position. The dorsal loop 106 extends from the outer convex surface of the plate body 102 to facilitate the threading of cerclage material, such as suture tape, fibertape, or wire, around the device. The dorsal loop 106 retains the cerclage material centered on the plate upon tightening to evenly secure the plate firmly against the bone under tension.

The invention can be fabricated to comprise the plate body 102, buttress wings 104, dorsal loop 106, and holes 108 using conventional manufacturing methods such as welding, pressing, casting, machining and/or forging. A variety of materials may be used including, metallics (i.e. titanium, stainless steel), bio absorbables (i.e. Poly-L-Lactide PLLA) or non-absorbables (i.e. PEEK polymer). Additionally, the inner surface of the Winged Looped Plate 100 could be plasma coated or otherwise roughened for enhanced grip to bone.

Figure 4:
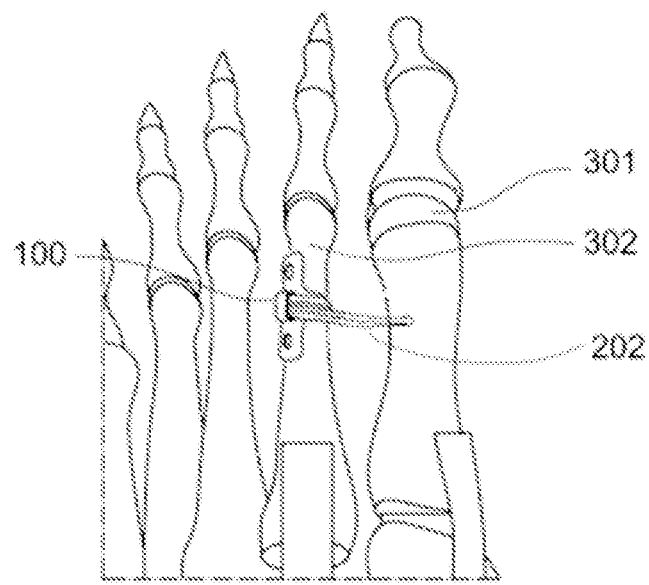
FIG. 4 is a top view of a skeleton embodying features of the present invention for a method and device for correcting bone deformities such as metatarsus primus adductus.
Figure 5:
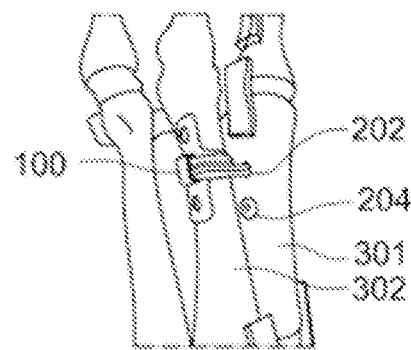
FIG. 5 is a profile view from the second metatarsal of a skeleton embodying features of the present invention for a method and device for correcting bone deformities such as metatarsus primus adductus.
Figure 6:
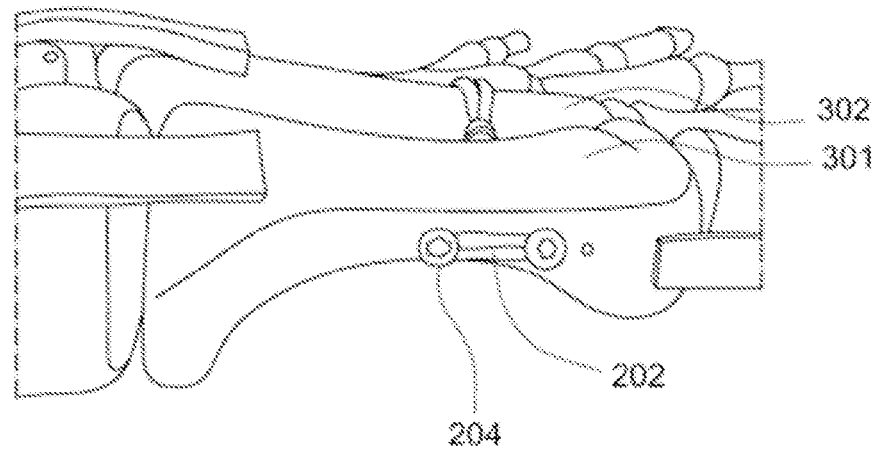
FIG. 6 is a profile view from the first metatarsal of a skeleton embodying features of the present invention for a method and device for correcting bone deformities such as metatarsus primus adductus.
Figure 9:
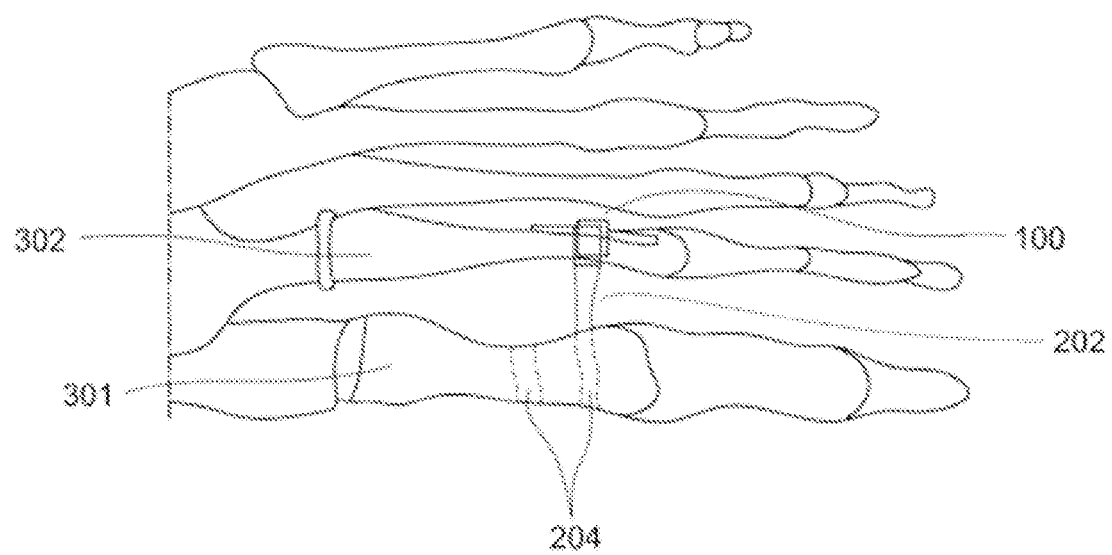
FIG. 9 is an illustration of the bone deformity, metatarsus primus adductus, anatomically reduced after the device and method of the present invention is applied.

FIG. 11 is a flowchart illustrating the correction of a bone deformity using the method and device of the present invention. First, an unstable bone 301 and a stable bone 302 near the unstable bone 301 is located (FIG. 4). Second, a hole to accommodate a tenodesis (interference type) screw 204 is drilled through the unstable bone 301 (FIG. 5) so that an opening is formed on the side of the unstable bone that is furthest away from the stable bone (FIG. 9). Third, a Winged Looped Plate 100 is placed with the inner surface against the stable bone 302 and with the dorsal loop 106 furthest away from the unstable bone 301 (FIG. 5). Fourth, a cerclage material 202 is passed through the dorsal loop 106 of the Winged Looped Plate 100 on the stable bone 302 and tied around the stable bone 302 and Winged Looped Plate 100 using a cerclage technique (FIG. 5). Fifth, the free ends of the cerclage material 202 are passed through the hole in the unstable bone 301 and tension is applied to the suture 202 to reduce the angular bone deformity (FIG. 6). Sixth, the cerclage material 202 is secured to the unstable bone 301 using a tenodesis (interference-type) screw 204 in the drill hole (FIG. 6).

Figure 7:
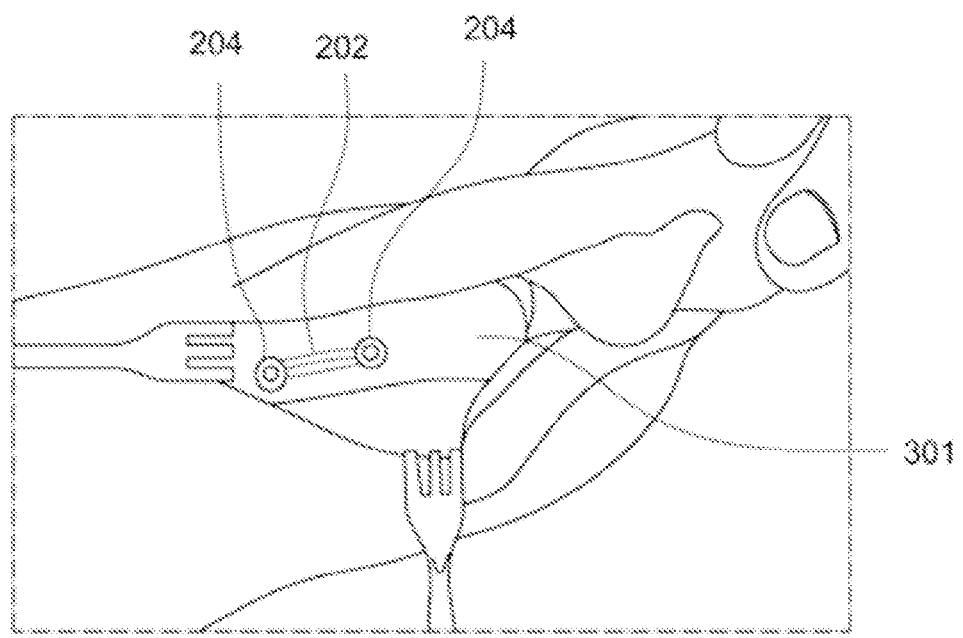
FIG. 7 is a profile view of a medial incision made along the first metatarsal with tenodesis (interference) screws anchoring the suture tape to the first metatarsal.

FIGS. 4-9 illustrate a method of using a Winged Looped Plate 100 to correct the angular bone deformity, metatarsus primus adductus. First, a medial incision is made along the first metatarsal 301 (the unstable bone) head and neck as best illustrated in FIG. 7. Second, a small incision is made dorsally over the second metatarsal 302 (the stable bone) neck. Third, blunt dissection is used to create a tunnel through the soft tissue between the first metatarsal 301 and second metatarsal 302, connecting the two incisions. Third, cerclage material 202 is passed through the tunnel from medial to lateral, and located through the dorsal incision where it is then threaded through the dorsal loop 106 of the Winged Looped Plate 100, which is then placed against the lateral cortex of the second metatarsal before the cerclage material 202 is tied once around the second metatarsal 302 using a cerclage technique, as best illustrated in FIGS. 4-5.

Figure 8:
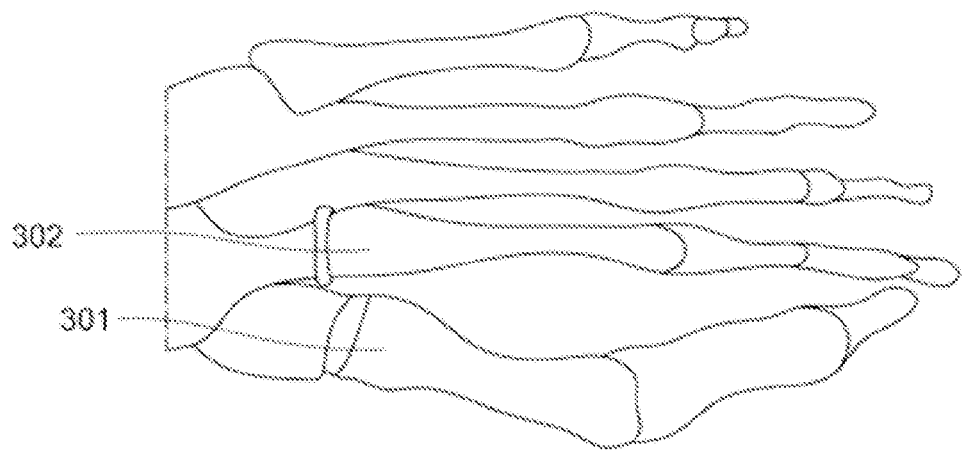
FIG. 8 is an illustration of the bone deformity, metatarsus primus adductus, before the device and method of the present invention is applied.

Fourth, the cerclage material 202 is tightened so that the Winged Looped Plate 100 is pressed firmly against the lateral aspect of the second metatarsal 302 and that buttress wings 104 of the plate cover and protect the dorsal and plantar cortices of the second metatarsal 302. The plate would be adhered to the bone primarily via tension from tightening the suture tape cerclage however, additional forms of optional fixation may include a single setscrew through a hole 108 in the dorsal wing 104, bone glue/paste/putty or other fixatives. Fifth, the free ends of the cerclage material 202 are then passed back through the soft tissue tunnel medially, then through a drill hole in the first metatarsal 301, from lateral to medial as illustrated in FIGS. 6-7. Sixth, the cerclage material 202 is pulled tightly through the drill hole, reducing the angular deformity to a more anatomic position, as illustrated in FIGS. 8-9. Seventh, a tenodesis anchor screw 204, shown in FIGS. 6-7, is inserted into the drill hole as an interference screw to maintain tension across the tethering mechanism between the first and second metatarsals. Finally, a second point of fixation can be achieved by passing the remaining cerclage material 202 end through a second drill hole in the first metatarsal and inserting a second tenodesis screw 204.

All features disclosed in this specification, including any accompanying claim, abstract, and drawings, may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. §112, paragraph 6. In particular, the use of "step of" in the claims herein is not intended to invoke the provisions of 35 U.S.C. §112, paragraph 6.

Although preferred embodiments of the present invention have been shown and described, various modifications and substitutions may be made thereto without departing from the spirit and scope of the invention. Accordingly, it is to be understood that the present invention has been described by way of illustration and not limitation.

What is claimed:

1. A winged looped plate device comprising:
   a plate body with an outer surface and an inner surface;
   at least one pair of buttress wings, each wing extending from an opposite side of the plate body and directly aligned with each other, such that a longitudinal axis of the pair of buttress wings is perpendicular to a longitudinal axis of the plate body; and
   at least one dorsal loop disposed on the outer surface of the plate body for threading of cerclage material through the at least one dorsal loop and tied around the device and a bone such that tension applied to the cerclage material secures the plate device to the bone to prevent displacement of the plate body,
   wherein the position of the at least one dorsal loop is immobile with respect to the plate body, and
   wherein the dorsal loop defines a channel, and an axis extending through the channel is perpendicular to the longitudinal axis of the plate body and is directly aligned with the longitudinal axis of the pair of buttress wings such that the cerclage material, once threaded through the at least one dorsal loop, extends along an axis perpendicular to the longitudinal axis of the plate body and is directly aligned with the longitudinal axis of the pair of buttress wings, and the cerclage material extends over an outer surface of each buttress wing along their longitudinal axis.

2. The winged looped plate device of claim 1, wherein the plate body comprises at least one hole for ingrowth of tissue.

3. The winged looped plate device of claim 1, wherein the at least one of the at least one pair of buttress wings comprises at least one hole for ingrowth of tissue.

4. The winged looped plate device of claim 1, wherein the plate body comprises at least one opening.

5. The winged looped plate device of claim 1, wherein at least one of the at least one pair of buttress wings comprises at least one opening.

6. The winged looped plate device of claim 1, wherein the at least one dorsal loop is disposed on the outer surface of the plate body at a point where the longitudinal axis of the pair of buttress wings and the longitudinal axis of the plate body intersect, so that cerclage material passing through the at least one dorsal loop is maintained centered along the outer surface of each buttress wing, and tension is applied evenly around the plate device when cerclage material is used to secure the plate to the bone to prevent displacement of the plate device.

7. The winged looped plate device of claim 1, further comprising a length of cerclage material.

8. A bone stabilization device comprising:
   an elongated plate body comprising:

a first surface facing in a first direction configured to face the bone;

a second surface facing in a second direction;

distal and proximal ends aligned along a longitudinal axis of the plate body; and first and second sides extending between the distal and proximal ends;

two buttress wings, each extending from one of the first and second sides at least partially along the first direction such that longitudinal axes of the two buttress wings are aligned with each other and perpendicular to the longitudinal axis of the plate body;

a transverse aperture disposed on the second surface of the plate body, the transverse aperture disposed in a central portion between the first and second sides, wherein the transverse aperture extends perpendicular to the longitudinal axis of the plate body and is directly aligned with the longitudinal axes of the two buttress wings, wherein the transverse aperture is configured to receive cerclage material therethrough, the cerclage material extending in a direction orthogonal to the longitudinal axis of the plate body such that the cerclage material passes directly over the two buttress wings.

9. The bone stabilization device of claim 8, wherein the plate is semi-tubular.

10. The bone stabilization device of claim 9, wherein the first surface is concave.

11. The bone stabilization device of claim 9, wherein the second surface is convex.

12. The bone stabilization device of claim 9, wherein the buttress wing extends curvature of the semi-tubular plate.

13. The bone stabilization device of claim 9, wherein a curvature of the semi-tubular plate is configured to receive a second metatarsal bone of human foot therein.

14. The bone stabilization device of claim 8, further comprising at least one hole on the plate body.

15. The bone stabilization device of claim 8, further comprising a length of cerclage material.

16. A bone plate device for reducing an angular bone deformity, comprising:

an elongate plate body configured to extend along a length of a patient's stable metatarsal, the elongate plate body comprising an inner surface configured to engage the stable metatarsal and an outer surface, wherein the elongate plate body comprises a first end and a second end and a longitudinal axis extending between the first end and the second end, wherein the longitudinal axis is configured to be parallel with the length of the stable metatarsal;

two buttress wings, each extending from an opposite side of the plate body such that both buttress wings share a longitudinal axis which is perpendicular to the longitudinal axis of the plate body, each of the buttress wings comprising an inner surface configured to engage the stable metatarsal and an outer surface, wherein the inner surfaces of the buttress wings at least partially face each other so that when the plate body and the buttress wings are placed against the stable metatarsal, the stable metatarsal is at least partially surrounded by the elongate plate body and the two buttress wings; and a transverse aperture located between the first and second ends of the plate body, wherein the transverse aperture defines a channel which extends perpendicular to the longitudinal axis of the plate body and is directly aligned along the longitudinal axis of the two buttress wings, such that when the plate body and the two buttress wings are placed against the stable metatarsal and cerclage material passes through the transverse aperture and is circumferentially tied around the plate device and underlying stable metatarsal, and is then secured to the patient's unstable metatarsal, the cerclage material extends directly over each of the two buttress wings.

17. The plate device of claim 16, wherein the plate device has a concave inner surface and a convex outer surface.

18. The plate device of claim 16, wherein the transverse aperture is defined at least in part by a dorsal loop located on or about the outer surface of the plate body.

19. The plate device of claim 18, wherein the dorsal loop is fixed and immobile relative to the plate body.

20. The plate device of claim 16, wherein the buttress wings are configured to shield the stable metatarsal bone by preventing cerclage material from directly contacting the stable metatarsal on the side of tension, and partially along adjacent cortices, thereby reducing a total area of contact between the cerclage material and underlying bone when cerclage material extends through the transverse aperture to secure the cerclage material around the plate and the patient's unstable metatarsal.

21. The plate device of claim 16, wherein the cerclage material extends entirely along the longitudinal axes of the two buttress wings.

* * * * *

UNITED STATES PATENT AND TRADEMARK OFFICE
CERTIFICATE OF CORRECTION

| | | |
|---|---|---|
| PATENT NO. | : 8,998,904 B2 | Page 1 of 1 |
| APPLICATION NO. | : 13/720826 | |
| DATED | : April 7, 2015 | |
| INVENTOR(S) | : Vladimir Zeetser et al. | |

It is certified that error appears in the above-identified patent and that said Letters Patent is hereby corrected as shown below:

In The Specification
In column 1, line 43, change "metatarsals," to --metatarsals.--.
In column 3, line 17, change "tie," to --tie.--.

In The Claims
In column 6, line 47, in claim 3, after "wherein" delete "the".
In column 7, line 34, in claim 13, after "a" delete "second".

Signed and Sealed this
Third Day of May, 2016

Michelle K. Lee
*Director of the United States Patent and Trademark Office*